United States Patent [19]
Slusher et al.

[11] Patent Number: 5,981,209
[45] Date of Patent: Nov. 9, 1999

[54] USE OF NAALADASE ACTIVITY TO IDENTIFY PROSTATE CANCER AND BENIGN PROSTATIC HYPERPLASIA

[75] Inventors: Barbara S. Slusher, Kingsville; Rena S. Lapidus, Baltimore, both of Md.

[73] Assignee: Guilford Pharmaceuticals Inc., Baltimore, Md.

[21] Appl. No.: 08/985,121

[22] Filed: Dec. 4, 1997

[51] Int. Cl.$^6$ ............................. C12Q 1/37; C12Q 1/34; G01N 33/53

[52] U.S. Cl. .............................. 435/23; 435/975; 435/24; 435/18; 435/4; 435/7.2; 435/7.21; 435/7.23

[58] Field of Search ................... 435/23, 975, 24, 435/18, 4, 7.2, 7.21, 7.23

[56] References Cited

U.S. PATENT DOCUMENTS

| | | | |
|---|---|---|---|
| H1312 | 5/1994 | Coughlin et al. | 435/23 |
| 4,151,172 | 4/1979 | Ondetti et al. | 435/23 |
| 4,168,267 | 9/1979 | Petrillo, Jr. | 435/23 |
| 4,316,896 | 2/1982 | Thorsett et al. | 435/23 |
| 4,337,201 | 6/1982 | Petrillo, Jr. | 435/23 |
| 4,374,131 | 2/1983 | Petrillo, Jr. | 435/23 |
| 4,444,765 | 4/1984 | Karanewsky et al. | 435/23 |
| 4,448,772 | 5/1984 | Karanewsky | 435/23 |
| 4,452,790 | 6/1984 | Karanewsky et al. | 435/23 |
| 4,452,791 | 6/1984 | Ryono et al. | 435/23 |
| 4,468,519 | 8/1984 | Krapcho | 435/23 |
| 4,547,324 | 10/1985 | Wong et al. | 435/23 |
| 4,555,506 | 11/1985 | Karanewsky et al. | 435/23 |
| 4,560,680 | 12/1985 | Ryono et al. | 435/23 |
| 4,560,681 | 12/1985 | Karanewsky | 435/23 |
| 4,567,166 | 1/1986 | Karanewsky et al. | 435/23 |
| 4,616,005 | 10/1986 | Karanewsky et al. | 435/23 |
| 4,671,958 | 6/1987 | Rodwell et al. | 435/23 |
| 4,703,043 | 10/1987 | Karanewsky et al. | 435/23 |
| 4,715,994 | 12/1987 | Parsons et al. | 435/23 |
| 4,716,155 | 12/1987 | Karanewsky et al. | 435/23 |
| 4,741,900 | 5/1988 | Alvarez et al. | 435/23 |

(List continued on next page.)

OTHER PUBLICATIONS

Stauch, B. et al., "The effects of N–acetylated alpha linked acidic dipeptidase (NAALADase) inhibitors on [$^3$H]NAAG catabolism in vivo," *Neuroscience Letters*, 100, p. 295–300 (1989).

Subasinghe, N. et al., "Synthesis of Acyclic and Dehydroaspartic Acid Analogues of Ac–Asp–Glu–OH and Their Inhibition of Rat Brain N–acetylated α–linked Acidic Dipeptidase (NAALA Dipeptidase)," *J. Med. Chem.*, 33, p. 2734–2744, (1990).

Rothstein, J. et al., "Abnormal excitatory amino acid metabolism in amyotrophic lateral sclerosis," *Anals of Neurology*, vol. 28, p. 18–25 (1990).

Slusher, B. et al., "Rat brain N–acetylated α–linked acidic dipeptidase activity," *The J. of Biological Chemistry*, vol. 265, No. 34, p. 21297–21301, (1990).

Tsai, G. et al., "Reductions in acidic amino acids and N–acetylaspartylglutamate in amyotrophic lateral sclerosis," *Brain Research*, 556, p. 151–161 (1991).

Coyle, J. et al., "N–acetyl–aspartyl glutamate," *Excitatory Amino Acids*, p. 69–77 (1990).

Meyerhoff, J. et al., "Genetically epilepsy–prone rats have increased brain regional activity of an enzyme which liberates glutamate from N–acetyl–aspartyl–glutamate," *Brain Research*, 593, p. 140–143 (1992).

(List continued on next page.)

*Primary Examiner*—Louise N. Leary
*Attorney, Agent, or Firm*—Gary M. Nath; Todd L. Juneau; Nath & Associates

[57] ABSTRACT

The present invention relates to novel methods and kits for quantitating N-Acetylated α-Linked Acidic Dipeptidase (NAALADase) enzyme activity in biological samples, including prostate biopsies, seminal fluid, ejaculate, prostatic fluid, blood, saliva, and urine, for the purpose of identifying and differentiating between prostate carcinoma, benign prostatic hyperplasia, and normal prostate.

42 Claims, 4 Drawing Sheets

U.S. PATENT DOCUMENTS

| | | |
|---|---|---|
| 4,849,525 | 7/1989 | Weller, III et al. ............... 435/23 |
| 4,853,326 | 8/1989 | Quash et al. ..................... 435/23 |
| 4,867,973 | 9/1989 | Goers et al. ..................... 435/23 |
| 4,885,283 | 12/1989 | Broadhurst et al. ............. 435/23 |
| 4,906,779 | 3/1990 | Weber et al. .................... 435/23 |
| 4,918,064 | 4/1990 | Cordi et al. ..................... 435/23 |
| 4,937,183 | 6/1990 | Ultee et al. ..................... 435/23 |
| 4,950,738 | 8/1990 | King et al. ...................... 435/23 |
| 4,959,493 | 9/1990 | Ohfume et al. .................. 435/23 |
| 4,962,097 | 10/1990 | Parsons et al. ................. 435/23 |
| 4,966,999 | 10/1990 | Coughlin et al. ................ 435/23 |
| 4,988,681 | 1/1991 | Ishikawa et al. ................ 435/23 |
| 4,994,446 | 2/1991 | SoKolovsky et al. ........... 435/23 |
| 5,030,732 | 7/1991 | Morita et al. ................... 435/23 |
| 5,041,644 | 8/1991 | Morita et al. ................... 435/23 |
| 5,047,227 | 9/1991 | Rodwell et al. ................. 435/23 |
| 5,061,806 | 10/1991 | Morita et al. ................... 435/23 |
| 5,093,525 | 3/1992 | Weber et al. .................... 435/23 |
| 5,099,063 | 3/1992 | Parsons et al. .................. 435/23 |
| 5,136,080 | 8/1992 | Miller et al. .................... 435/23 |
| 5,140,104 | 8/1992 | Coughlin et al. ................ 435/23 |
| 5,143,908 | 9/1992 | Parsons et al. .................. 435/23 |
| 5,145,990 | 9/1992 | Parsons et al. .................. 435/23 |
| 5,147,867 | 9/1992 | Parsons et al. .................. 435/23 |
| 5,156,840 | 10/1992 | Goers et al. ..................... 435/23 |
| 5,162,504 | 11/1992 | Horoszewicz ................... 435/23 |
| 5,162,512 | 11/1992 | King et al. ...................... 435/23 |
| 5,190,976 | 3/1993 | Weber et al. .................... 435/23 |
| 5,196,510 | 3/1993 | Rodwell et al. ................. 435/23 |
| 5,242,915 | 9/1993 | Ueda et al. ...................... 435/23 |
| 5,262,568 | 11/1993 | Weber et al. .................... 435/23 |
| 5,326,856 | 7/1994 | Coughlin et al. ................ 435/23 |
| 5,336,689 | 8/1994 | Weber et al. .................... 435/23 |
| 5,449,761 | 9/1995 | Belinka, Jr. et al. ............ 435/23 |
| 5,474,547 | 12/1995 | Aebischer et al. ............... 435/23 |
| 5,495,042 | 2/1996 | Belinka, Jr. et al. ............ 435/23 |
| 5,508,273 | 4/1996 | Beers et al. ..................... 435/23 |
| 5,527,885 | 6/1996 | Coughlin et al. ................ 435/23 |
| 5,538,957 | 7/1996 | Tsaklakidis et al. ............. 435/23 |
| 5,672,592 | 9/1997 | Jackson et al. .................. 435/23 |
| 5,698,402 | 12/1997 | Luderer et al. .................. 435/23 |

OTHER PUBLICATIONS

Meyerhoff, J. et al., "Activity of a NAAG–hydrolyzing enzyme in brain may affect seizure susceptibility in genetically epilepsy–prone rats," *Molecular Neurobiology of Epilepsy*, p. 163–172 (1992).

Slusher, B. et al., "Immunocytochemical localization of the N–acetyl–aspartyl–glutamate (NAAG) hydrolyzing enzyme N–acetylated α–linked acidic dipeptidase (NAALADase)," *J. of Comp. Neurology*, 315, p. 217–229 (1992).

Tsai, G. et al., "Immunocytochemical distribution of N–acetylaspartylglutamate in the rat forebrain and glutamergic pathways," *J. of Chem. Neuroanatomy*, 6, p. 277–292 (1993).

Tsai, G. et al., "Changes of excitatory neurotransmitter metabolism in schizophrenic brains," *Salmon Lecturer of the New York Academy of Medicine*, (Dec. 2–3, 1993).

Slusher, B. et al., "NAALADase: A Potential Regulator of Synaptic Glutamate," *Biotech Update DuPont NEN*, 9, p. 37–39 (1994).

Koenig, M. et al., "N–acetyl–aspartyl–glutamate (NAAG) elicits rapid increase in intraneuronal $Ca^{2+}$ in vitro," *NeuroReports*, 5, p. 1063–1068 (1994).

Jackson, P. et al., "Design, synthesis, and biological activity of a potent inhibitor of the neuropeptidase N–acetylated α–linked acidic dipeptidase," *J. of Medicinal Chemistry*, (1995).

Vornov, J. et al., "Toxic NMDA–receptor activation occurs during recovery in a tissue culture model of ischemia," *J. of Neurochemistry*, 65, p. 1681–1691 (1995).

Woods, D. et al., "Gender–linked injury after focal cerebral ischemia," *Soc. For Neuroscience 1996 Abstract Form*, (1996).

Bhardwaj, A. et al., "Striatal nitric oxide (NO) production is enhanced in focal cerebral ischemia: An in vivo microdialysis study," *Soc. For Neuroscience 1996 Abstract Form*, (1996).

Heston, W., "Bedeutung des prostataspezifischen Membranantigens (PSMA)," *Urologe*, 35, p. 400–407 (1996).

Carter, R. et al., "Prostate–specific membrane antigen is a hydrolase with substrate and pharmacologic characteristics of neuropeptidase," *Proc. Nat. Acad. Sci.*, 93, p. 749–753 (1996).

Carter et al; Proc. Natl. Acad. Sci. U.S.A. (1996), vol. 93(2), p. 749–753.

USE OF NAALADASE ACTIVITY TO IDENTIFY PROSTATE CANCER AND BENIGN PROSTATIC HYPERPLASIA

BACKGROUND OF THE INVENTION

1. Field of the Invention

The present invention relates generally to the field of prostate cancer, and particularly, to methods and kits for assaying NAALADase activity in a sample to differentiate between prostate cancer, benign prostatic hyperplasia (BPH), and normal prostate tissue.

2. Description of the Prior Art

Prostate Cancer

Prostate cancer is the leading form of cancer and the second leading cause of death from cancer for men in the United States. The American Cancer Society has estimated that in 1996 alone, 317,100 new cases of prostate cancer were diagnosed and 41,400 deaths were caused by prostate cancer. The incidence rate of prostate cancer increased 65% between 1980 and 1990, and will continue to rise with improved screening tests and longer life expectancies. While most men used to die of other illnesses before prostate cancer had a chance to develop, higher prostate cancer mortality rates are expected as men live longer and the disease has more time to progress.

There is a recognized need for earlier, more effective means of detection of malignant prostate cancer, since only 3–4% of all prostate carcinomas are currently detected by routine screening (Brawer et al., 1992).

Currently available diagnostic techniques include pathohistology of prostate biopsies, digital rectal examination (DRE), transrectal ultrasonography (TRUS), and assaying prostate-specific antigen.

Pathohistology of prostate tissue can definitively identify prostate cancer in many cases. However, there are limitations to this method of screening. First, the Gleason's grading scale used by pathologists is at best semi-quantitative since it may be difficult to search every cell of every tissue slice. Second, one pathologist's thresholds of scoring often do not coincide with the scores given by other pathologists. For these reasons Gleason scores themselves have limited quantitative value.

DRE and TRUS are widely employed by diagnosticians but are very limited in their ability to diagnose prostate cancer and do not provide the ability to distinguish benign prostatic hyperplasia and prostate cancer.

Assaying for PSA in a patient's serum has been shown to be a good predictor of prostate cancer. However, a commonly cited difficulty with this tool is that both prostate cancer and BPH give rise to elevated PSA values. A study of the rate of PSA elevation over many months and years shows that PSA elevates at a slightly higher rate in prostate cancer versus BPH. However, the work is retrospective and the patients have to wait years before the outcome is apparent. Accordingly, the diagnostician cannot easily and quickly differentiate between prostate cancer and BPH using PSA values.

NAALADase and the CNS

NAAG and NAALADase have been historically implicated in several human and animal pathological conditions relating to the CNS. For example, it has been demonstrated that intra-hippocampal injections of NAAG elicit prolonged seizure activity. More recently, it was reported that rats genetically prone to epileptic seizures have a persistent increase in their basal level of NAALADase activity. These observations support the hypothesis that increased availability of synaptic glutamate elevates seizure susceptibility, and suggest that NAALADase inhibitors may provide anti-epileptic activity.

NAAG and NAALADase have also been implicated in the pathogenesis of ALS and in the pathologically similar animal disease called Hereditary Canine Spinal Muscular Atrophy (HCSMA). It has been shown that concentrations of NAAG and its metabolites—NAA, glutamate and aspartate—are elevated two- to three-fold in the cerebrospinal fluid of ALS patients and HCSMA dogs. Additionally, NAALADase activity is significantly increased (two- to three-fold) in post-mortem spinal cord tissue from ALS patients and HCSMA dogs. As such, NAALADase inhibitors may be clinically useful in curbing the progression of ALS if increased metabolism of NAAG is responsible for the alterations of CSF levels of these acidic amino acids and peptides.

Abnormalities in NAAG levels and NAALADase activity have also been documented in post-mortem schizophrenic brain, specifically in the prefrontal and limbic brain regions.

NAALADase and the Prostate

In 1993, the molecular cloning of Prostate Specific Membrane Antigen (PSMA) was reported as a potential prostate carcinoma marker and hypothesized to serve as a target for imaging and cytotoxic treatment modalities for prostate cancer. This lead to the testing of NAALADase inhibitors on the growth of LNCAP cells (a cancer cell line). PSMA antibodies, particularly indium-111 labelled and itrium labelled PSMA antibodies, have been described and examined clinically for the diagnosis and treatment of prostate cancer. PSMA is expressed in prostatic ductal epithelium and is present in seminal plasma, prostatic fluid and blood of prostate cancer patients. Surprisingly, it was found in 1996 that the expression of PSMA CDNA confers the activity of NAALADase.

However, prior to the present invention it has not been shown that the native PSMA enzyme in the prostate actually exhibits NAALADase activity, nor has NAALADase activity been found to be an indicator of the development of prostate tumors or to have any correlation to the pathological state of prostate tissue.

Despite many recent advances in the diagnosis of prostate cancer, it is evident that there exists no fast, reliable, or efficient method for differentiating between prostate cancer and BPH. The current lack of knowledge in the area of diagnosing abnormal prostate cell growth makes patient prognosis uncertain and complicates clinical treatment decisions.

SUMMARY OF THE INVENTION

Accordingly, the present invention is based upon the surprising discovery that NAALADase activity can be used to differentiate between normal prostate tissue, benign prostatic hyperplasia (BPH), and prostate cancer.

In particular, the present invention is directed to a method for detecting or identifying benign prostatic hyperplasia (BPH) or prostate cancer, comprising: comparing NAALADase activity in a sample of prostate tissue or bodily fluid to a reference which correlates to NAALADase activity in normal prostate tissue, benign prostatic hyperplasia, or prostate cancer, whereby differential NAALADase activity between the NAALADase activity in the sample of prostate tissue or bodily fluid and the reference which correlates to NAALADase activity in normal prostate tissue, benign prostatic hyperplasia (BPH), or prostate cancer detects or identifies benign prostatic hyperplasia (BPH) or prostate cancer.

The present invention also relates to a method for detecting or identifying benign prostatic hyperplasia (BPH) or prostate cancer, comprising: assaying NAALADase activity in a sample of prostate tissue or bodily fluid; and comparing the NAALADase activity in the sample of prostate tissue or bodily fluid to a reference which correlates to NAALADase activity in normal prostate tissue, benign prostatic hyperplasia, or prostate cancer, whereby differential NAALADase activity between the NAALADase activity in the sample of prostate tissue or bodily fluid and the reference which correlates to NAALADase activity in normal prostate tissue, benign prostatic hyperplasia (BPH), or prostate cancer detects or identifies benign prostatic hyperplasia (BPH) or prostate cancer.

The present invention also provides a method for detecting or identifying a pathological condition of prostate tissue, comprising: assaying a sample of prostate tissue or a bodily fluid for NAALADase activity; and comparing the NAALADase activity of the sample of prostate tissue or bodily fluid to known NAALADase activity for normal prostate, benign prostatic hyperplasia, or prostate cancer, whereby differential NAALADase activity between the sample of prostate tissue or bodily fluid and the normal prostate, benign prostatic hyperplasia, or prostate cancer detects or identifies the pathological condition of the prostate tissue.

The present invention further includes a method for detecting or identifying benign prostatic hyperplasia or prostate cancer, comprising measuring or assaying NAALADase activity in a sample of prostate tissue or bodily fluid wherein the NAALADase activity on a detectable or labeled substrate of NAALADase results in a quantity of detectable or labeled metabolite; and comparing the quantity of labeled metabolite from the sample of prostate tissue or bodily fluid to at least one reference or control wherein the reference or control represents a quantity of labeled metabolite from prostate tissue or bodily fluid which is indicative of non-neoplastic conditions, and whereby differential activity between the detectable or labeled metabolite from the sample of prostate tissue or bodily fluid and the control or reference quantity of labeled metabolite from normal prostate tissue or bodily fluid detects or identifies benign prostatic hyperplasia or prostate cancer.

The present invention is additionally directed to a method for detecting or identifying differential NAALADase activity in a sample of prostate tissue or bodily fluid, comprising: comparing NAALADase activity in a sample of prostate tissue or bodily fluid to a reference which correlates to NAALADase activity in normal prostate tissue, benign prostatic hyperplasia, or prostate cancer, whereby comparing NAALADase activity between the sample of prostate tissue or bodily fluid and the reference which correlates to NAALADase activity in normal prostate tissue, benign prostatic hyperplasia (BPH), or prostate cancer detects or identifies differential NAALADase activity.

The present invention further relates to a method for detecting or identifying differential NAALADase activity in both the membrane and cytosolic fractions of a sample of prostate tissue or bodily fluid, comprising: comparing the ratio of membrane NAALADase activity to cytosolic NAALADase activity in a sample of prostate tissue or bodily fluid to a reference which correlates to the ratio of membrane NAALADase activity to cytosolic NAALADase activity in normal prostate tissue, benign prostatic hyperplasia, or prostate cancer, whereby comparing NAALADase activity between the sample of prostate tissue or bodily fluid and the reference which correlates to the ratio of membrane NAALADase activity to cytosolic NAALADase activity in normal prostate tissue, benign prostatic hyperplasia (BPH), or prostate cancer detects or identifies differential NAALADase activity.

Preferrably, the NAALADase activity in normal prostate tissue, benign prostatic hyperplasia, or prostate cancer is a quantitative value of a detectable metabolite of NAALADase activity wherein the detectable metabolite results from NAALADase activity on a substrate selected from the group consisting of N-Acetyl Aspartyl Glutamate (NAAG), folate polyglutamate, derivatives thereof, and substrates labeled with a radioactive marker, chemiluminescent marker, enzymatic marker, chromogenic marker, or other detectable marker.

Another preferred aspect of the present invention includes a series of standards which indicate a quantitative value of a detectable metabolite of NAALADase activity, and in particular where the series of standards provides a gradient from lowest to highest NAALADase activity wherein benign prostatic hyperplasia exhibits a lower quantitative value of the detectable metabolite than normal prostate tissue and wherein prostate cancer exhibits a higher quantitative value of the detectable metabolite than normal prostate tissue.

Another preferred aspect of the present invention includes bodily fluids which are selected from the group consisting of seminal vesicle fluid, ejaculate, prostatic fluid, blood, saliva, and urine.

The present invention is also directed to kits for performing the assays and methods disclosed herein. In one preferred embodiment, a kit is provided for detecting or identifying benign prostatic hyperplasia (BPH) or prostate cancer in a sample of prostate tissue or bodily fluid, comprising: a detectable NAALADase enzyme substrate packaged in a container; and a reference which correlates to NAALADase activity in normal prostate tissue, benign prostatic hyperplasia, or prostate cancer, whereby differential NAALADase activity between NAALADase activity in the sample of prostate tissue or bodily fluid and the reference which correlates to NAALADase activity in normal prostate tissue, benign prostatic hyperplasia (BPH), or prostate cancer detects or identifies benign prostatic hyperplasia (BPH) or prostate cancer.

Another kit of the present invention is provided for detecting or identifying a pathological condition of a prostate in a sample of prostate tissue or bodily fluid, comprising: a detectable NAALADase enzyme substrate packaged in a container; and a reference which correlates to NAALADase activity in normal prostate tissue, benign prostatic hyperplasia, or prostate cancer, whereby differential NAALADase activity between NAALADase activity in the sample of prostate tissue or bodily fluid and the reference which correlates to NAALADase activity in normal prostate tissue, benign prostatic hyperplasia (BPH), or prostate cancer detects or identifies benign prostatic hyperplasia (BPH) or prostate cancer.

Yet another preferred kit of the present invention is provided for detecting or identifying differential NAALADase activity in a sample of prostate tissue or bodily fluid, comprising: a detectable NAALADase enzyme substrate packaged in a container; and a reference which correlates to NAALADase activity in normal prostate tissue, benign prostatic hyperplasia, or prostate cancer.

A further kit of the present invention is provided for detecting or identifying differential NAALADase activity in both the membrane and cytosolic fractions of a sample of prostate tissue or bodily fluid, comprising: a detectable NAALADase enzyme substrate packaged in a container; and a reference which correlates to a ratio of membrane NAALADase activity to cytosolic NAALADase activity in normal prostate tissue, benign prostatic hyperplasia, or prostate cancer.

In preferred kits, the substrate is selected from the group consisting of N-Acetyl Aspartyl Glutamate (NAAG), folate polyglutamate, derivatives thereof, and substrates labeled with a radioactive marker, chemiluminescent marker, enzymatic marker, chromogenic marker, or other detectable marker.

Also in preferred kits of the present invention, the reference which correlates to NAALADase activity in normal prostate tissue, benign prostatic hyperplasia, or prostate cancer is a series of standards showing a gradient from lowest to highest NAALADase activity wherein benign prostatic hyperplasia exhibits a lower quantitative value of the detectable metabolite than normal prostate tissue and wherein prostate cancer exhibits a higher quantitative value of the detectable metabolite than normal prostate tissue.

The present inventive kits also provide for the testing of bodily fluids which are selected from the group consisting of seminal vesicle fluid, blood, saliva, ejaculate, prostatic fluid, and urine.

DETAILED DESCRIPTION OF THE INVENTION

Definitions

Figure 1:
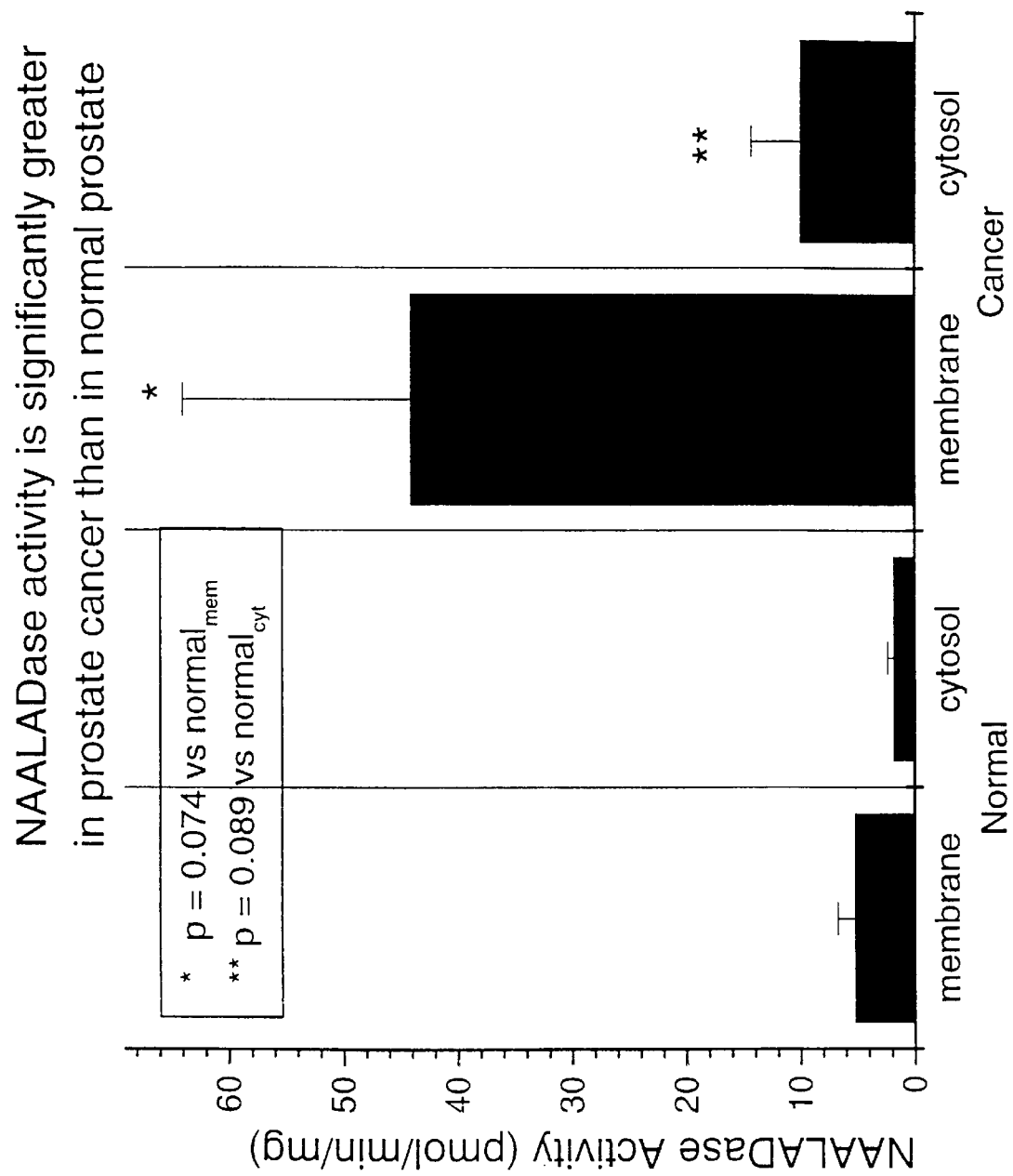
FIG. 1 is a bar graph showing that NAALADase enzyme activity (picomoles/minute/milligram) is remarkably significantly greater in prostate cancer ($\approx$45 pmol/min/mg) than in normal prostate tissue (5 pmol/min/mg).

"NAAG" refers to N-acetyl-aspartyl-glutamate, an important peptide component in the body. Studies suggest that NAAG may function as a neurotransmitter and/or neuromodulator in the central nervous system, or as a precursor of the neurotransmitter glutamate.

"NAALADase" refers to N-acetylated α-linked acidic dipeptidase, a membrane-bound metallopeptidase which catabolizes NAAG to N-acetylaspartate (NAA) and glutamate:

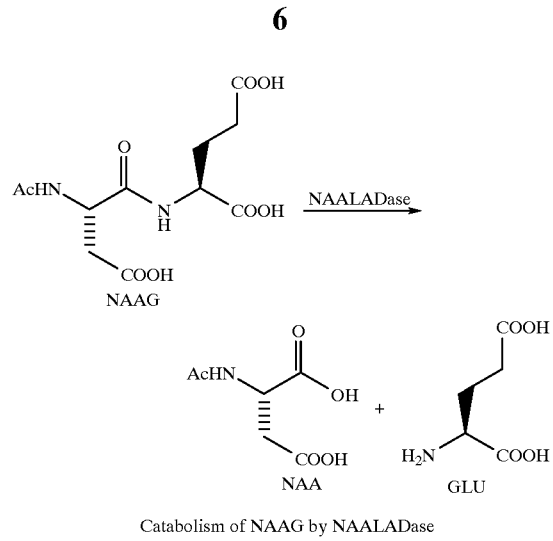

Catabolism of NAAG by NAALADase

Km of 540 nM. If NAAG is a bioactive peptide, then NAALADase may serve to inactivate NAAG'S synaptic action. Alternatively, if NAAG functions as a precursor for glutamate, the primary function of NAALADase may be to regulate synaptic glutamate availability.

"Prostate disease" refers to any disease, disorder or condition of the prostate, including prostate cancer, such as adenocarcinoma or metastatic cancers, and conditions characterized by abnormal growth of prostatic epithelial cells, such as benign prostatic hyperplasia.

"PSA" refers to Prostate Specific Antigen, a well known prostate cancer marker. It is a protein produced by prostate cells and is frequently present at elevated levels in the blood of men with prostate cancer. PSA correlates with tumor burden, serves as an indicator of metastatic involvement, and provides a parameter for following a prostate cancer patient's response to surgery, irradiation and androgen replacement therapy.

"PSMA" refers to Prostate Specific Membrane Antigen, a potential prostate carcinoma marker that has been hypothesized to serve as a target for imaging and cytotoxic treatment modalities for prostate cancer. PSMA is expressed in prostatic ductal epithelium and is present in seminal plasma, prostatic fluid and blood of cancer patients. It has been found that the expression of PSMA cDNA confers the activity of NAALADase.

LNCaP: an epithelial cell line derived from a human prostate tumor, which is androgen sensitive. The LNCaP cell line was derived from a supraclavicular lymph node metastashs of a human prostate carcinoma. Cells of this line exhibit increased proliferation in response to androgen, in vitro, and they secrete prostate specific antigen (PSA), a marker of differentiated epithelial cells.

IDENTIFYING: in the context of identifying BPH, prostate adenocarcinoma, or other form of prostate cancer, ascertaining, establishing or otherwise determining one or more factual characteristics of benign prostatic hyperplasia, prostatic adenocarcinoma, or other form of prostate cancer.

METHODS OF USE OF THE PRESENT INVENTION

Protocol for Assaying NAALADase Enzyme Activity in Biological Samples

Fresh or frozen (−80° C.) samples were resuspended in 10x volume of ice cold bakers water and minced by polytron. Following sonication, the sample preparation was centrifuged at 50,000×g at 4° C. for 20 min. The supernatant (cytosolic fraction) was removed, divided into 1 ml aliquots and frozen at −80° C. The pellet was then resuspended in half the original volume of 50 mM Tris Cl buffer. This membrane fraction was again minced by polytron, sonicated and divided into 1 ml aliquots and frozen at −80° C. The NAALADase assay was performed as described by Slusher et al. (J. Biol. Chemistry 265:21297–21301, 1990). Briefly, $CoCl_2$ and tris-HCl pH 7.4 was added to known volumes of sample. Following the addition of N-acetyl-aspartate-L--$^3$H-glutamate (NAAG), the sample was incubated at 37° C. for 15 min and then passed through an ion exchange column to separate aspartate from the labeled glutamate [flow through]. The samples are then counted on a Beckman LS 6000 beta scintillation counter. The assay is followed by a Biorad protein assay to determine specific activity for each sample.

The present invention relates to novel methods and kits for quantifying N-Acetylated α-Linked Acidic Dipeptidase (NAALADase) enzyme activity in biological samples, and more particularly, to differentiate between prostate carcinoma, benign prostatic hyperplasia and normal prostate. The present invention provides methods for quantitating NAALADase enzyme activity in biological samples, including prostate tissue, ejaculate, urine, blood, tears, lymph, sweat, saliva, sputum, seminal vesicle fluid, sperm, prostatic fluid, and assaying for the quantitative amount of NAALADase enzyme activity present in the sample.

The present invention contemplates using a variety of NAALADase enzyme substrates to measure the NAALADase enzyme activity in a biological sample. These substrates specifically include N-acetyl aspartyl glutamate, folate polyglutamate, and derivatives of the same labeled with radioactive, chemiluminescent, and enzymatic markers.

The detection systems that can be used in the process according to the present invention include radioactivity scintillation counters, immunometric detection systems, calorimetric or densitometric based assays, spectrographic based assays, and analytical chromatographic assays.

The present invention further includes methods and kits for early identification of prostate cancer and benign prostatic hyperplasia by measuring the NAALADase enzyme activity of the fluids, excretions, secretions and cells of the urogenitary tract and comparing this NAALADase enzyme activity to the differential NAALADase enzyme activity values known for normal prostate, benign prostatic hyperplasia, and prostate cancer thereby providing a reliable differential diagnostic indicator of prostate pathology.

The present invention also relates to methods and kits for quantifying the NAALADase enzyme activity in membrane and cytosolic fractions of prostate tissue, and using the ratio of membrane/cytosolic NAALADase enzyme activity to differentiate between benign prostatic hyperplasia and prostate cancer.

The present invention also contemplates using the measured NAALADase activity to differentiate between prostate cancers which respond to hormone therapy treatments and prostate cancers which do not respond to hormone therapy treatments. In addition, the present invention contemplates using the measured NAALADase activity to differentiate between non-metastatic prostate cancers and metastatic prostate cancers.

The present invention also contemplates using the measured NAALADase activity to screen for cancer recurrence or cancer metastasis in prostate cancer patients undergoing cancer treatment.

The present invention also contemplates a change in NAALADase enzyme activity through the modification of cellular machinery, inducer-suppressor proteins, nucleic acids, and compounds affecting the same.

FIG. 1 is a bar graph showing that NAALADase enzyme activity (picomoles/minute/milligram) is remarkably significantly greater in prostate cancer (≈45 pmol/min/mg) than in normal prostate tissue (5 pmol/min/mg). Prostates are removed from men undergoing radical prostatectomies as treatment for prostate cancer. After evaluation by a pathologist, the prostates were separated histologically into normal, BPH and tumor sections. The frozen tissue samples were resuspended in 10× volume of ice cold bakers water and minced by polytron. Following sonication, the tissue preparation was centrifuged at 50,000×g at 4° C. for 20 min. The supernatant (cytosolic fraction) was removed, divided into 1 ml aliquots and frozen at −80° C. The pellet was then resuspended in half the original volume of 50 mM Trisl Cl buffer. This membrane fraction was again minced by polytron, sonicated and divided into 1 ml aliquots and frozen at −80° C. The NAALADase assay was performed as described by Slusher et al. (J. Biol. Chemistry 265:21297–21301, 1990). Briefly, $CoCl_2$ and tris-HCl pH 7.4 was added to known volumes of tissue extract. Following the addition of N-acetyl-aspartate-L--$^3$H-glutamate (NAAG), the sample was incubated at 37° C. for 15 min and then passed through an ion exchange column to separate aspartate from the labeled glutamate [flow through]. The samples are then counted on a Beckman LS 6000 beta scintillation counter. The assay is followed by a Biorad protein assay to determine specific activity for each sample as a measure of picomoles of labeled glutamate per minute of incubated exposure of labeled substrate to NAALADase enzyme per milligram of prepared sample exposed to substrate.

Figure 2:
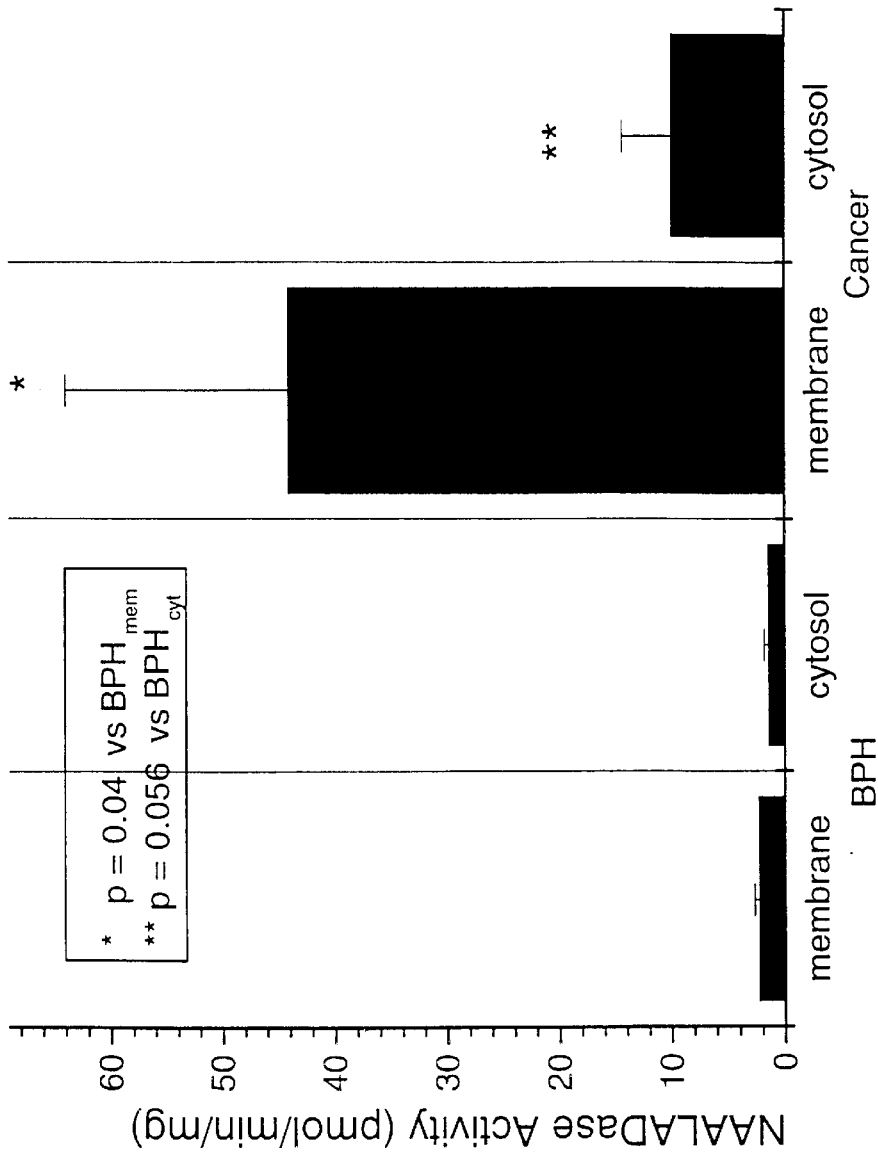
FIG. 2 is a bar graph showing that NAALADase enzyme activity (picomoles/minute/milligram) is surprisingly significantly greater in prostate cancer ($\approx$45 pmol/min/mg) than in benign prostatic hyperplasia ($\approx$2 pmol/min/mg).

FIG. 2 is a bar graph showing that NAALADase enzyme activity (picomoles/minute/milligram) is surprisingly significantly greater in prostate cancer (≈45 pmol/min/mg) than in benign prostatic hyperplasia (≈2 pmol/min/mg). The protocol employed for preparing and measuring the NAALADase enzyme activity of the prostate specimens were the same as described above for FIG. 1.

Figure 3:
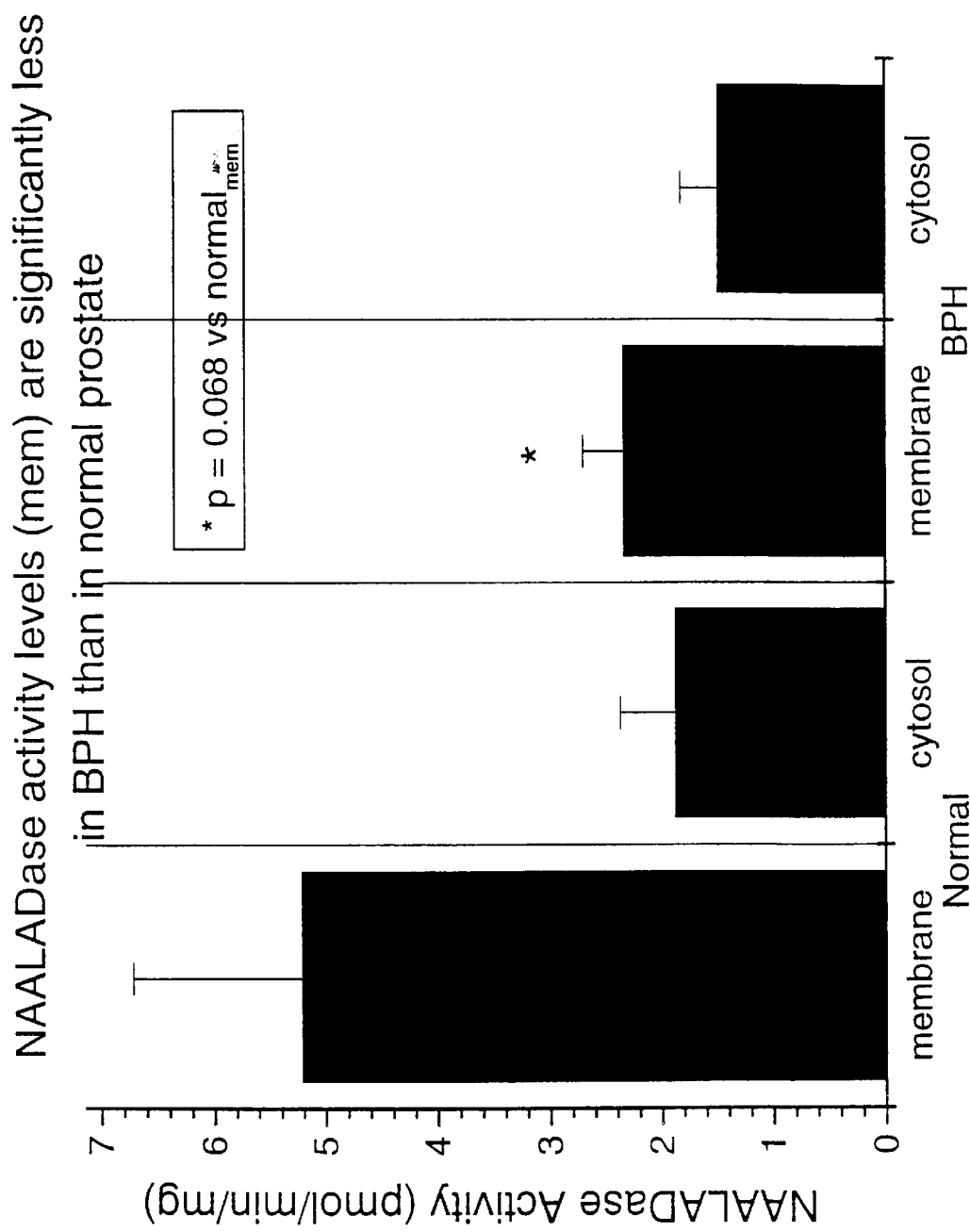
FIG. 3 is a bar graph showing that NAALADase enzyme activity (picomoles/minute/milligram) in benign prostatic hyperplasia ($\approx$2 pmol/min/mg) is significantly less than in normal prostate tissue ($\approx$5 pmol/min/mg).

FIG. 3 is a bar graph showing that NAALADase enzyme activity (picomoles/minute/milligram) in benign prostatic hyperplasia (≈2 pmol/min/mg) is significantly less than in normal prostate tissue (≈5 pmol/min/mg). The protocol employed for preparing and measuring the NAALADase enzyme activity of the prostate specimens were the same as described above for FIG. 1.

Figure 4:
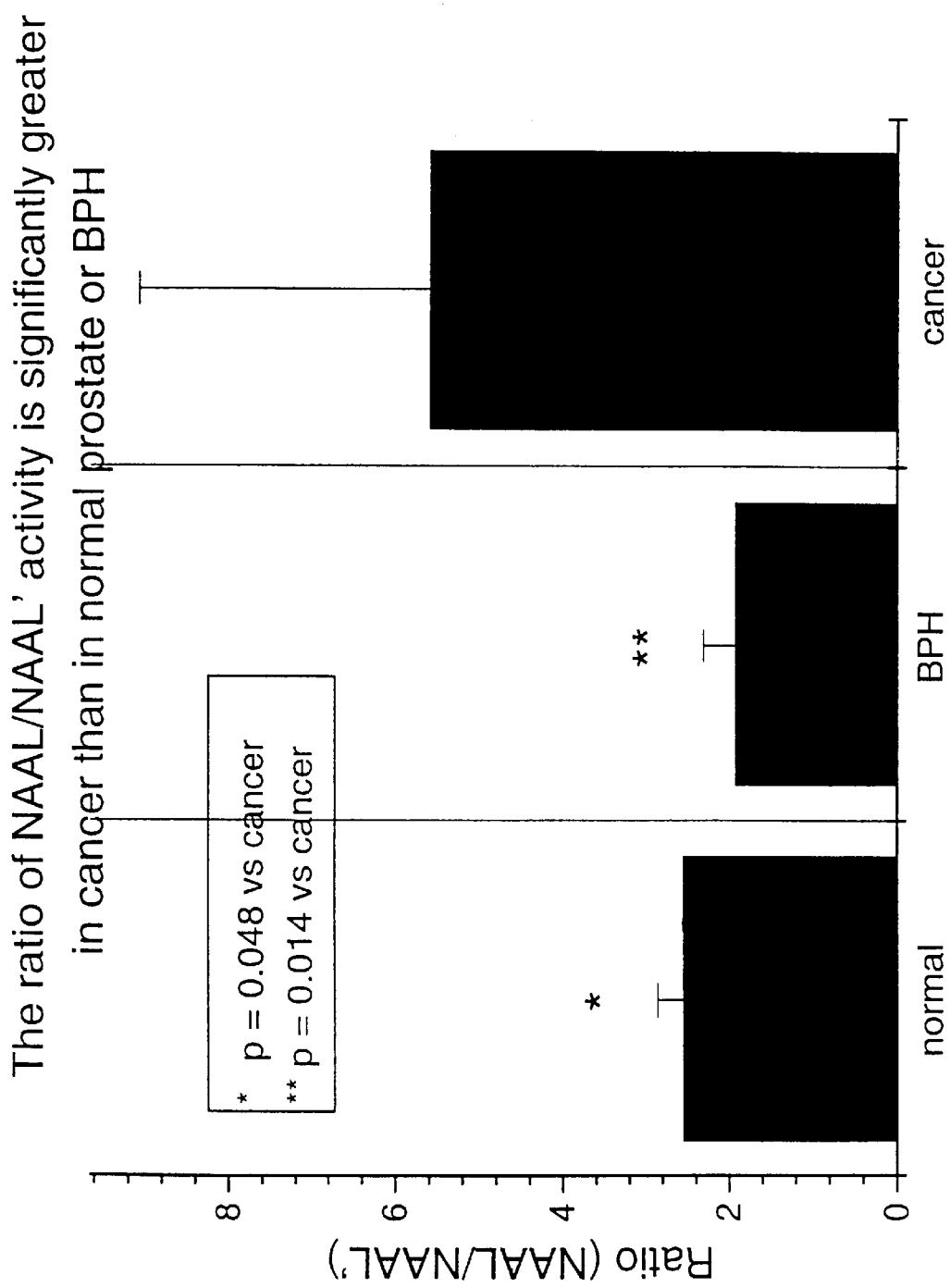
FIG. 4 is a bar graph showing that the ratio of membrane versus cytosolic NAALADase enzyme activity is especially significantly greater in prostate cancer (ratio$\approx$5.9) than in benign prostatic hyperplasia (ratio$\approx$2.0) or normal prostate tissue (ratio$\approx$2.3).

FIG. 4 is a bar graph showing that the ratio of membrane versus cytosolic NAALADase enzyme activity is especially significantly greater in prostate cancer (ratio≈5.9) than in benign prostatic hyperplasia (ratio≈2.0) or normal prostate tissue (ratio≈2.3). The protocol employed for preparing and measuring the NAALADase enzyme activity of the prostate specimens were the same as described above for FIG. 1.

EXAMPLES

The following examples are illustrative of the present invention and are not intended to be limitations thereon. Unless otherwise indicated, all percentages are based upon 100% by weight of the final composition.

Example 1

Assaying NAALADase Activity in Prostate Tissue of Prostate Cancer Patients

Prostates are removed from men undergoing radical prostatectomies as treatment for prostate cancer. After evaluation by a pathologist, the prostates were separated histologically into normal, BPH and tumor sections. The frozen tissue samples were resuspended in 10× volume of ice cold bakers water and minced by polytron. Following sonication, the tissue preparation was centrifuged at 50,000×g at 4° C. for 20 min. The supernatant (cytosolic fraction) was removed, divided into 1 ml aliquots and frozen at −80° C. The pellet was then resuspended in half the original volume of 50 mM Trisl Cl buffer. This membrane fraction was again minced by polytron, sonicated and divided into 1 ml aliquots and frozen at −80° C. The NAALADase assay was performed as described by Slusher et al. (J. Biol. Chemistry 265:21297–21301, 1990). Briefly, $CoCl_2$ and tris-HCl pH 7.4 was added to known volumes of tissue extract. Following the addition of N-acetyl-aspartate-L-$^3$H-glutamate (NAAG), the sample was incubated at 37° C. for 15 min and then passed through an ion exchange column to separate aspartate from the labeled glutamate [flow through]. The samples are then counted on a Beckman LS 6000 beta scintillation counter. The assay is followed by a Biorad protein assay to determine specific activity for each sample.

Example 2

Assaying NAALADase Activity in Prostate Tissue to Identify the Absence of Neoplastic Disease A patient submits a prostate biopsy sample for analysis. The sample is assayed according to the method described on pages 16–17. It would be expected that normal prostate tissue results indicate a lack of neoplastic disease.

Example 3

Assaying NAALADase Activity in Prostate Tissue to Identify the Presence of Benign Prostatic Hyperplasia A patient submits a prostate biopsy sample for analysis. The sample is assayed according to the method described on pages 16–17. It would be expected that benign prostatic hyperplasia tissue results indicate a lack of prostate cancer.

Example 4

Assaying NAALADase Activity in Prostate Tissue to Differentiate Between the Presence of Prostate Cancer, Benign Prostatic Hyperplasia, and Normal Prostate A patient submits a prostate biopsy sample for analysis. The sample is assayed according to the method described on pages 16–17. It would be expected that prostate cancer tissue results indicate a lack of benign prostatic hyperplasia. A patient whose prostate biopsy indicates the occurrence of prostate cancer and not benign prostatic hyperplasia would likely undergo aggressive treatment regimens including prostatectomy, radiation therapy, and chemotherapy.

Example 5

Assaying NAALADase Activity in Ejaculate to Identify the Absence of Neoplastic Disease A patient submits an ejaculate sample for analysis. The sample is assayed according to the method described on pages 16–17. It would be expected that normal prostate results indicate a lack of neoplastic disease.

Example 6

Assaying NAALADase Activity in Ejaculate to Identify the Presence of Benign Prostatic Hyperplasia A patient submits an ejaculate sample for analysis. The sample is assayed according to the method described on pages 16–17. It would be expected that benign prostatic hyperplasia results indicate a lack of prostate cancer.

Example 7

Assaying NAALADase Activity in Ejaculate to Differentiate Between the Presence of Prostate Cancer, Benign Prostatic Hyperplasia, and Normal Prostate A patient submits an ejaculate sample for analysis. The sample is assayed according to the method described on pages 16–17. It would be expected that prostate cancer results indicate a lack of benign prostatic hyperplasia. A patient whose ejaculate indicates the occurrence of prostate cancer and not benign prostatic hyperplasia would likely undergo aggressive treatment regimens including prostatectomy, radiation therapy, and chemotherapy.

Example 8

Assaying NAALADase Activity in Ejaculate to Differentiate Between the Presence of Hormone-Responsive Prostate Cancer and Hormone-Refractory Prostate Cancer A patient submits an ejaculate sample for analysis. The sample is assayed according to the method described on pages 16–17. It would be expected that prostate cancer results could be further differentiated between hormone-responsive prostate cancer and hormone-refractory prostate cancer.

Example 9

Assaying NAALADase Activity in Ejaculate to Differentiate Between the Presence of Metastatic Prostate Cancer and Non-Metastatic Prostate Cancer A patient submits an ejaculate sample for analysis. The sample is assayed according to the method described on pages 16–17. It would be expected that prostate cancer results could be further differentiated between metastatic prostate cancer and non-metastatic prostate cancer.

Example 10

Assaying NAALADase Activity in Ejaculate from a Patient Who Has Undergone Treatment for Prostate Cancer to Detect the Recurrence of Cancer A patient undergoing treatment for prostate cancer, or who has previously undergone treatment for prostate cancer, submits an ejaculate sample for analysis. The sample is assayed according to the method described on pages 16–17. It would be expected that a prostate cancer result would indicate the recurrence of prostate cancer.

Example 11

Assaying NAALADase Activity in Urine to Identify the Absence of Neoplastic Disease A patient submits a urine sample for analysis. The sample is assayed according to the method described on pages 16–17. It would be expected that normal prostate results indicate a lack of neoplastic disease.

Example 12

Assaying NAALADase Activity in Prostate Tissue to Identify the Presence of Benign Prostatic Hyperplasia A patient submits a urine sample for analysis. The sample is assayed according to the method described on pages 16–17. It would be expected that benign prostatic hyperplasia results indicate a lack of prostate cancer.

Example 13

Assaying NAALADase Activity in Urine to Differentiate Between the Presence of Prostate Cancer, Benign Prostatic Hyperplasia, and Normal Prostate A patient submits a urine sample for analysis. The sample is assayed according to the method described on pages 16–17. It would be expected that prostate cancer results indicate a lack of benign prostatic hyperplasia. A patient whose urine NAALADase enzyme activity indicates the occurrence of prostate cancer and not benign prostatic hyperplasia would likely undergo aggressive treatment regimens including prostatectomy, radiation therapy, and chemotherapy.

Example 14

Assaying NAALADase Activity in Prostate Tissue Using the Diagnostic Kit Disclosed by the Present Invention to Identify the Absence of Neoplastic Disease A patient submits a prostate biopsy sample for analysis. The sample is assayed using the diagnostic kit employing the method described on pages 16–17. It would be expected that normal prostate tissue results indicate a lack of neoplastic disease.

Example 15

Assaying NAALADase Activity in Prostate Tissue Using the Diagnostic Kit Disclosed by the Present Invention to Identify the Presence of Benign Prostatic Hyperplasia A patient submits a prostate biopsy sample for analysis. The sample is assayed using the diagnostic kit employing the method described on pages 16–17. It would be expected that benign prostatic hyperplasia tissue results indicate a lack of prostate cancer.

Example 16

Assaying NAALADase Activity in Prostate Tissue Using the Diagnostic Kit Disclosed by the Present Invention to Differentiate Between the Presence of Prostate Cancer, Benign Prostatic Hyperplasia, and Normal Prostate A patient submits a prostate biopsy sample for analysis. The sample is assayed using the diagnostic kit employing the method described on pages 16–17. It would be expected that prostate cancer tissue results indicate a lack of benign prostatic hyperplasia. A patient whose prostate biopsy indicates the occurrence of prostate cancer and not benign prostatic hyperplasia would likely undergo aggressive treatment regimens including prostatectomy, radiation therapy, and chemotherapy.

Example 17

Assaying NAALADase Activity in Ejaculate Using the Diagnostic Kit Disclosed by the Present Invention to Differentiate Between the Presence of Prostate Cancer, Benign Prostatic Hylerplasia, and Normal Prostate A patient submits an ejaculate sample for analysis. The sample is assayed using the diagnostic kit employing the method described on pages 16–17. A patient with a normal prostate would be expected to have ejaculate with NAALADase enzyme value near 5 pmol/min/mg, while the presence of BPH would reveal a NAALADase enzyme value near 2 pmol/min/mg. It would be expected that prostate cancer would result in a NAALADase enzyme value near 45 pmol/min/mg. A patient whose ejaculate indicates the occurrence of prostate cancer and not benign prostatic hyperplasia would likely undergo aggressive treatment regimens including prostatectomy, radiation therapy, and chemotherapy.

Example 18

Assaying NAALADase Activity in Urine Using the Diagnostic Kit Disclosed by the Present Invention to Differentiate Between the Presence of Prostate Cancer, Benign Prostatic Hyperplasia, and Normal Prostate A patient submits a urine sample for analysis. The sample is assayed using the diagnostic kit employing the method described on pages 16–17. A patient with a normal prostate would be expected to have urine with NAALADase enzyme value near 5 pmol/min/mg, while the presence of BPH would reveal a NAALADase enzyme value near 2 pmol/min/mg. It would be expected that prostate cancer would result in a NAAALADase enzyme value near 45 pmol/min/mg. A patient whose urine indicates the occurrence of prostate cancer and not benign prostatic hyperplasia would likely undergo aggressive treatment regimens including prostatectomy, radiation therapy, and chemotherapy.

The invention being thus described, it will be obvious that the same may be varied in many ways. Such variations are not to be regarded as a departure from the spirit and scope of the invention and all such modification are intended to be included within the scope of the following claims.

What is claimed:

1. A method for detecting or identifying benign prostatic hyperplasia (BPH) or prostate cancer, comprising: adding a NAALADase enzyme substrate or a NAALADase inhibitor to a sample of prostate tissue or bodily fluid; incubating the sample of prostate tissue or bodily fluid; assaying NAALADase activity in the sample of prostate tissue or bodily fluid; and comparing the NAALADase activity in the sample of prostate tissue or bodily fluid to a reference which correlates to NAALADase activity in normal prostate tissue, benign prostatic hyperplasia, or prostate cancer to detect or identify differential NAALADase activity, whereby differential NAALADase activity between the NAALADase activity in the sample of prostate tissue or bodily fluid and the reference which correlates to NAALADase activity in normal prostate tissue, benign prostatic hyperplasia (BPH), or prostate cancer detects or identifies benign prostatic hyperplasia (BPH) or prostate cancer.

2. The method of claim 1, wherein the reference which correlates to NAALADase activity in normal prostate tissue, benign prostatic hyperplasia, or prostate cancer is a quantitative value of a detectable metabolite of NAALADase activity.

3. The method of claim 2, wherein the detectable metabolite results from NAALADase activity on a substrate selected from the group consisting of N-Acetyl Aspartyl Glutamate (NAAG), folate polyglutamate, derivatives thereof, and substrates labeled with a radioactive marker, chemiluminescent marker, enzymatic marker, chromogenic marker, or other detectable marker.

4. The method of claim 1, wherein the reference which correlates to NAALADase activity in normal prostate tissue, benign prostatic hyperplasia, or prostate cancer is a series of standards which indicate a quantitative value of a detectable metabolite of NAALADase activity.

5. The method of claim 4, wherein the series of standards which indicate a quantitative value of the detectable metabolite is a gradient from lowest to highest NAALADase activity wherein benign prostatic hyperplasia exhibits a lower quantitative value of the detectable metabolite than normal prostate tissue and wherein prostate cancer exhibits a higher quantitative value of the detectable metabolite than normal prostate tissue.

6. The method of claim 1, wherein the bodily fluid is selected from the group consisting of seminal vesicle fluid, ejaculate, prostatic fluid, blood, saliva, and urine.

7. A method for detecting or identifying a pathological condition of prostate tissue, comprising: adding a NAALADase enzyme substrate or a NAALADase inhibitor to a sample of prostate tissue or bodily fluid; incubating the sample of prostate tissue or bodily fluid; assaying the sample of prostate tissue or a bodily fluid for NAALADase activity; and comparing the NAALADase activity of the sample of prostate tissue or bodily fluid to known NAALADase activity for normal prostate, benign prostatic hyperplasia, or prostate cancer to detect or identify differential NAALADase activity, whereby differential NAALADase activity between the sample of prostate tissue or bodily fluid and the normal prostate, benign prostatic hyperplasia, or prostate cancer detects or identifies the pathological condition of the prostate tissue.

8. The method of claim 7, wherein the pathological condition of the prostate is benign prostatic hyperplasia or prostate cancer.

9. The method of claim 7, wherein the known NAALADase activity is a quantitative value of a detectable metabolite of NAALADase activity.

10. The method of claim 9, wherein the detectable metabolite results from NAALADase activity on a substrate selected from the group consisting of N-Acetyl Aspartyl Glutamate (NAAG), folate polyglutamate, derivatives thereof, and substrates labeled with a radioactive marker, chemiluminescent marker, enzymatic marker, chromogenic marker, or other detectable marker.

11. The method of claim 7, wherein the known NAALADase activity is a series of standards which indicate a quantitative value of a detectable metabolite of NAALADase activity.

12. The method of claim 11, wherein the series of standards which indicate a quantitative value of the detectable metabolite is a gradient from lowest to highest NAALADase activity wherein benign prostatic hyperplasia exhibits a lower quantitative value of the detectable metabolite than normal prostate tissue and wherein prostate cancer exhibits a higher quantitative value of the detectable metabolite than normal prostate tissue.

13. The method of claim 7, wherein the bodily fluid is selected from the group consisting of seminal vesicle fluid, ejaculate, prostatic fluid, blood, saliva, and urine.

14. A method for detecting or identifying benign prostatic hyperplasia or prostate cancer, comprising measuring or assaying NAALADase activity in a sample of prostate tissue or bodily fluid wherein the NAALADase activity on a detectable or labeled substrate of NAALADase activity on a detectable or labeled substrate of NAALADase added to a sample of prostate tissue or bodily fluid, and incubated with the sample of prostate tissue or bodily fluid, results in a quantity of detectable or labeled metabolite; and comparing the quantity of labeled metabolite from the sample of prostate tissue or bodily fluid to at least one reference or control wherein the reference or control represents a quantity of labeled metabolite from prostate tissue or bodily fluid which is indicative of non-neoplastic conditions to detect or identify differential NAALADase activity, and whereby differential activity between the detectable or labeled metabolite from the sample of prostate tissue or bodily fluid and the control or reference quantity of labeled metabolite from normal prostate tissue or bodily fluid detects or identifies benign prostatic hyperplasia or prostate cancer.

15. The method of claim 14, wherein the substrate is selected from the group consisting of N-Acetyl Aspartyl Glutamate (NAAG), folate polyglutamate, derivatives thereof, and substrates labeled with a radioactive marker, chemiluminescent marker, enzymatic marker, chromogenic marker, or other detectable marker.

16. The method of claim 14, wherein the reference or control is a series of standards which is a gradient from lowest to highest NAALADase activity wherein benign prostatic hyperplasia exhibits a lower quantitative value of the detectable metabolite than normal prostate tissue and wherein prostate cancer exhibits a higher quantitative value of the detectable metabolite than normal prostate tissue.

17. The method of claim 14, wherein the bodily fluid is selected from the group consisting of seminal vesicle fluid, ejaculate, prostatic fluid, blood, saliva, and urine.

18. A method for detecting or identifying differential NAALADase activity in a sample of prostate tissue or bodily fluid, comprising: adding a NAALADase enzyme substrate or a NAALADase inhibitor to a sample of prostate tissue or bodily fluid; incubating the sample of prostate tissue or bodily fluid; assaying NAALADase activity in the sample of prostate tissue or bodily fluid; and comparing NAALADase activity in the sample of prostate tissue or bodily fluid to a reference which correlates to NAALADase activity in normal prostate tissue, benign prostatic hyperplasia, or prostate cancer, whereby comparing NAALADase activity between the sample of prostate tissue or bodily fluid and the reference which correlates to NAALADase activity in normal prostate tissue, benign prostatic hyperplasia (BPH), or prostate cancer detects or identifies differential NAALADase activity.

19. The method of claim 18, wherein the reference which correlates to NAALADase activity in normal prostate tissue, benign prostatic hyperplasia, or prostate cancer is a quantitative value of a detectable metabolite of NAALADase activity.

20. The method of claim 19, wherein the detectable metabolite results from NAALADase activity on a substrate selected from the group consisting of N-Acetyl Aspartyl Glutamate (NAAG), folate polyglutamate, derivatives thereof, and substrates labeled with a radioactive marker, chemiluminescent marker, enzymatic marker, chromogenic marker, or other detectable marker.

21. The method of claim 18, wherein the reference which correlates to NAALADase activity in normal prostate tissue, benign prostatic hyperplasia, or prostate cancer is a series of standards which indicate a quantitative value of a detectable metabolite of NAALADase activity.

22. The method of claim 21, wherein the series of standards which indicate a quantitative value of the detectable metabolite is a gradient from lowest to highest NAALADase activity wherein benign prostatic hyperplasia exhibits a lower quantitative value of the detectable metabolite than normal prostate tissue and wherein prostate cancer exhibits a higher quantitative value of the detectable metabolite than normal prostate tissue.

23. The method of claim 18, wherein the bodily fluid is selected from the group consisting of seminal vesicle fluid, ejaculate, prostatic fluid, blood, saliva, and urine.

24. A method for detecting or identifying differential NAALADase activity in both the membrane and cytosolic fractions of a sample of prostate tissue or bodily fluid, comprising: adding a NAALADase enzyme substrate to membrane and cytosolic fractions of a sample of prostate tissue or bodily fluid; incubating the sample of prostate tissue or bodily fluid; assaying NAALADase activity in the sample of prostate tissue or bodily fluid; and comparing the ratio of membrane NAALADase activity to cytosolic NAALADase activity in the sample of prostate tissue or bodily fluid to a reference which correlates to the ratio of membrane NAALADase activity to cytosolic NAALADase activity in normal prostate tissue, benign prostatic hyperplasia, or prostate cancer, whereby comparing NAALADase activity between the sample of prostate tissue or bodily fluid and the reference which correlates to the ratio of membrane NAALADase activity to cytosolic NAALADase activity in normal prostate tissue, benign prostatic hyperplasia (BPH), or prostate cancer detects or identifies differential NAALADase activity.

25. The method of claim 24, wherein the reference which correlates to NAALADase activity in normal prostate tissue, benign prostatic hyperplasia, or prostate cancer is a quantitative value of a detectable metabolite of NAALADase activity.

26. The method of claim 25, wherein the detectable metabolite results from NAALADase activity on a substrate selected from the group consisting of N-Acetyl Aspartyl Glutamate (NAAG), folate polyglutamate, derivatives thereof, and substrates labeled with a radioactive marker, chemiluminescent marker, enzymatic marker, chromogenic marker, or other detectable marker.

27. The method of claim 24, wherein the reference which correlates to NAALADase activity in normal prostate tissue, benign prostatic hyperplasia, or prostate cancer is a series of standards which indicate a quantitative value of a detectable metabolite of NAALADase activity.

28. The method of claim 27, wherein the series of standards which indicate a quantitative value of the detectable metabolite is a gradient from lowest to highest NAALADase activity wherein benign prostatic hyperplasia exhibits a lower quantitative value of the detectable metabolite than normal prostate tissue and wherein prostate cancer exhibits a higher quantitative value of the detectable metabolite than normal prostate tissue.

29. The method of claim 24, wherein the bodily fluid is selected from the group consisting of seminal vesicle fluid, ejaculate, prostatic fluid, blood, saliva, and urine.

30. A kit for detecting or identifying a pathological condition of a prostate in a sample of prostate tissue or bodily fluid, comprising: a detectable NAALADase enzyme substrate packaged in a container; and a reference which correlates to NAALADase activity in normal prostate tissue, benign prostatic hyperplasia, or prostate cancer, whereby differential NAALADase activity between NAALADase activity in the sample of prostate tissue or bodily fluid and the reference which correlates to NAALADase activity in normal prostate tissue, benign prostatic hyperplasia (BPH), or prostate cancer detects or identifies benign prostatic hyperplasia (BPH) or prostate cancer.

31. The kit of claim 30, wherein the substrate is selected from the group consisting of N-Acetyl Aspartyl Glutamate (NAAG), folate polyglutamate, derivatives thereof, and substrates labeled with a radioactive marker, chemiluminescent marker, enzymatic marker, chromogenic marker, or other detectable marker.

32. The kit of claim 30, wherein the reference which correlates to NAALADase activity in normal prostate tissue, benign prostatic hyperplasia, or prostate cancer is a series of standards showing a gradient from lowest to highest NAALADase activity wherein benign prostatic hyperplasia exhibits a lower quantitative value of the detectable metabolite than normal prostate tissue and wherein prostate cancer exhibits a higher quantitative value of the detectable metabolite than normal prostate tissue.

33. The kit of claim 30, wherein the bodily fluid is selected from the group consisting of seminal vesicle fluid, ejaculate, prostatic fluid, blood, saliva, and urine.

34. A kit for detecting or identifying differential NAALADase activity in a sample of prostate tissue or bodily fluid, comprising: a detectable NAALADase enzyme substrate packaged in a container; and a reference which correlates to NAALADase activity in normal prostate tissue, benign prostatic hyperplasia, or prostate cancer.

35. The kit of claim 34, wherein the substrate is selected from the group consisting of N-Acetyl Aspartyl Glutamate (NAAG), folate polyglutamate, derivatives thereof, and substrates labeled with a radioactive marker, chemiluminescent marker, enzymatic marker, chromogenic marker, or other detectable marker.

36. The kit of claim 34, wherein the reference which correlates to NAALADase activity in normal prostate tissue, benign prostatic hyperplasia, or prostate cancer is a series of standards showing a gradient from lowest to highest NAALADase activity wherein benign prostatic hyperplasia exhibits a lower quantitative value of the detectable metabolite than normal prostate tissue and wherein prostate cancer exhibits a higher quantitative value of the detectable metabolite than normal prostate tissue.

37. The method of claim 34, wherein the bodily fluid is selected from the group consisting of seminal vesicle fluid, ejaculate, prostatic fluid, blood, saliva, and urine.

38. A kit for detecting or identifying differential NAALADase activity in both the membrane and cytosolic fractions of a sample of prostate tissue or bodily fluid, comprising: a detectable NAALADase enzyme substrate packaged in a container; and a reference which correlates to a ratio of membrane NAALADase activity to cytosolic NAALADase activity in normal prostate tissue, benign prostatic hyperplasia, or prostate cancer.

39. The kit of claim 38, wherein the substrate is selected from the group consisting of N-Acetyl Aspartyl Glutamate (NAAG), folate polyglutamate, derivatives thereof, and substrates labeled with a radioactive marker, chemiluminescent marker, enzymatic marker, chromogenic marker, or other detectable marker.

40. The kit of claim 38, wherein the reference which correlates to NAALADase activity in normal prostate tissue, benign prostatic hyperplasia, or prostate cancer is a series of standards showing a gradient from lowest to highest NAALADase activity wherein benign prostatic hyperplasia exhibits a lower quantitative value of the detectable metabolite than normal prostate tissue and wherein prostate cancer exhibits a higher quantitative value of the detectable metabolite than normal prostate tissue.

41. The kit of claim 38, wherein the bodily fluid is selected from the group consisting of seminal vesicle fluid, ejaculate, prostatic fluid, blood, saliva, and urine.

42. The kit of claim 40, wherein the pathological condition of a prostate is benign prostatic hyperplasia (BPH) or prostate cancer.

* * * * *

UNITED STATES PATENT AND TRADEMARK OFFICE
CERTIFICATE OF CORRECTION

PATENT NO. : 5,981,209
DATED : November 9, 1999
INVENTOR(S) : Barbara S. SLUSHER et al.

It is certified that error appears in the above-indentified patent and that said Letters Patent is hereby corrected as shown below:

Claim 14, column 13, lines 62-63, after "detectable or labeled substrate of NAALADase" and before "added to a", please remove "activity on a detectable or labeled substrate of NAALADase".

Claim 42, column 16, line 62, after "The kit of claim" and before ", wherein the pathological", please replace "40" with --30--.

Signed and Sealed this

Ninth Day of May, 2000

Attest:

Attesting Officer

Q. TODD DICKINSON

Director of Patents and Trademarks